United States Patent [19]
Wildermann

[11] Patent Number: 5,908,957
[45] Date of Patent: Jun. 1, 1999

[54] ISOMERIZATION PROCESS

[75] Inventor: Angela Wildermann, Bad Säckingen, Germany

[73] Assignee: Roche Vitamins Inc., Parsippany, N.J.

[21] Appl. No.: 09/013,456

[22] Filed: Jan. 26, 1998

[30] Foreign Application Priority Data

Feb. 14, 1997 [EP] European Pat. Off. .............. 97102394

[51] Int. Cl.$^6$ ........................... C07C 69/74; C07C 61/22; C07C 62/30
[52] U.S. Cl. ......................... 560/128; 562/510; 564/191; 568/443; 568/668; 568/824
[58] Field of Search ........................ 560/128; 562/510; 564/191; 568/443, 668, 824

[56] References Cited

U.S. PATENT DOCUMENTS

| | | | |
|---|---|---|---|
| 3,384,633 | 5/1968 | Kardys et al. ................. | 260/207.1 |
| 3,838,029 | 9/1974 | Fischer et al. .................. | 204/159 |
| 4,026,778 | 5/1977 | Lalonde et al. ................. | 204/159 |
| 4,051,174 | 9/1977 | Stoller et al. ................... | 560/234 |

FOREIGN PATENT DOCUMENTS 1 468 798    11/1970    Germany .

OTHER PUBLICATIONS

Chernysh et al., Mechanism of the . . . vitamin A acetate, Zh. Org. Khim. vol. 11(7), pp. 1400–1403, 1975.

Mulry et al., Isomerization of retinyl . . . solvents, J. Assoc. Off. Anal. Chem. vol. 66 (3), pp. 746–750, 1983.

Lukton et al., On the Amine–Catalyzed . . . Aldehydes, J. Am. Chem. Soc. vol. 106, pp. 258–259, Jan. 1984.

Derwent Abstract of Japanese Patent No. 05 009 482 A, Nov. 9, 1993.

E. L. Eliel, Stereochemie der Kohlenstoffverbindungen, pp. 410–415, (1966).

Abstract of German Patent Specification 1 468 798, Nov. 19, 1970.

*Primary Examiner*—Samuel Barts
*Assistant Examiner*—Rosalynd Keys
*Attorney, Agent, or Firm*—George W. Johnston; Dennis P. Tramaloni

[57] ABSTRACT

A process is disclosed for the catalyzed isomerization of a Z-isomer of a vitamin A compound or of a mixture of several of such isomers into a mixture of the corresponding all-E- and 13-Z-isomers of this vitamin A compound. The process utilizes nitrogen monoxide or a gas mixture containing nitrogen monoxide as the isomerization catalyst. Vitamin A acetate or vitamin A acid is preferably used as the vitamin A compound. The thus-produced all-E vitamin A and its alkanoyl esters have of all isomers by far the highest biological activity and are accordingly almost exclusively used in human and animal nutrition. The 13-Z-vitamin A compounds in turn play an important role as pharmaceutically active substances.

12 Claims, No Drawings

ISOMERIZATION PROCESS

BACKGROUND OF THE INVENTION

The present invention is concerned with a novel process for the catalyzed isomerization of vitamin A compounds using nitrogen monoxide as the isomerization catalyst. In particular, the invention is concerned with the isomerization of undesired isomers of vitamin A compounds, e.g., the 9-Z-, 11-Z-, 9,13-di-Z- and 11,13-di-Z-vitamin A compounds individually or as a mixture of these isomers, into a corresponding mixture of the useful all-E- and 13-Z compounds, which are by necessity present in equilibrium.

In natural vitamin A, as is contained in many fish liver oils, e.g., shark, cod, halibut and Californian jewfish liver oil, the total content of vitamin A consists of about 65% of all-E vitamin A and about 35% of 13-Z-vitamin A. The all-E-vitamin A and its alkanoyl esters have, of all isomers, by far the highest biological activity and are accordingly almost exclusively used in human and animal nutrition. On the other hand, the 13-Z-vitamin A compounds also play an important role, namely as pharmaceutically active substances.

The vitamin A preparations commercialized at present are almost exclusively produced synthetically. Since the previously known and used processes for the production of a vitamin A compound do not yield pure all-E compound, but only mixtures of various isomers having more or less large amounts of the all-E isomer, there has hitherto always been the problem of the isomerization of the various undesired isomers to the all-E isomer. The problem is firstly to achieve yields of all-E compounds which are as high as possible and also—since the total Z→E conversion is not possible—to obtain mixtures from which the all-E isomer can be isolated in a manner which is as simple as possible.

The method most used previously was the isomerization with iodine in the presence of pyridine [see, for example, German Auslegeschrift (DAS) 1 468 798]. The addition of pyridine is necessary in order to keep the formation of the 9-Z isomer as low as possible. However, this method has the disadvantage that the iodine must be removed as completely as possible from the reaction mixture after the isomerization and prior to the isolation of the all-E compound. This is usually carried out by the addition of an iodine reducing agent, such as, for example, sodium thiosulphate, sodium bisulphite or sodium borohydride, the excess of which is subsequently removed by washing, filtration or other suitable methods.

Photochemical isomerization using sensitizers is also known (see, for example, DAS 2 210 800). However, this method is encumbered with the disadvantage that the sensitizer must be removed after completion of the isomerization. Moreover, the photochemical isomerization (not only with, but also without sensitizers) requires complex and expensive special apparatuses, which can lead to considerable difficulties especially when working on an industrial scale.

SUMMARY OF THE INVENTION

The object of the present invention is, starting from the pure Z-isomers or also any isomer mixtures, even in the presence of impurities, to obtain a mixture having a content of the corresponding all-E-vitamin A compound which is as high as possible and from which the all-E isomer, and the 13-Z isomer which is unavoidably present with this isomer in equilibrium, can be isolated readily without great expense in a form which is as pure as possible. It has now surprisingly been found that this object can be achieved by catalysis with gaseous nitrogen monoxide (NO), especially at atmospheric pressure or under a slight over-pressure. The isomerization catalyst NO is removed by replacing the NO atmosphere or simply by de-pressurizing the reaction mixture. The isolation of the all-E and of the 13-Z isomer can then be effected according to methods known per se, e.g., cooling crystallization or evaporation crystallization. A very stable product is produced using this isomerization process. No special apparatuses are required.

DETAILED DESCRIPTION OF THE INVENTION

The present invention is accordingly a process for the catalyzed isomerization of a Z-isomer of a vitamin A compound or of a mixture of several of such isomers to a mixture of the corresponding all-E and 13-Z isomers of this vitamin A compound, which process comprises using nitrogen monoxide or a gas mixture containing nitrogen monoxide as the catalyst for the isomerization. Because the all-E and 13-Z isomers will finally exist after completion of equilibration in an about 2:1 (by weight) equilibrium, the final concentration of all-E vitamin A compound produced by the process of the invention cannot exceed about 67%, and is often less due to the presence of other isomers and impurities in the reaction mixture. If the ratio of all-E to 13-Z in the reaction mixture is greater than about 2:1, the process in accordance with the invention will actually cause a reduction in the concentration of the all-E isomer but an increase in the concentration of the 13-Z isomer (see Example 4).

Thus, the present invention is directed to a process for the catalyzed isomerization of a Z isomer of a vitamin A compound into a mixture of the all-E and 13-Z isomers of the vitamin A compound, which process comprises contacting a reaction mixture comprising the Z isomer of the vitamin A compound with nitrogen monoxide under conditions of temperature and NO pressure sufficient to isomerize the Z isomer to the mixture of the all-E and 13-Z isomers.

Under the term "vitamin A compounds" there are to be understood in the scope of the present invention vitamin A itself (retinol), vitamin A aldehyde (retinal) and vitamin A acid and their derivatives, e.g., esters, acetals and amides. Such derivatives within the scope of the present invention are those which have vitamin A biological activity. The term embraces especially the following compounds of formula I in which no indication of the stereoisomerism is given:

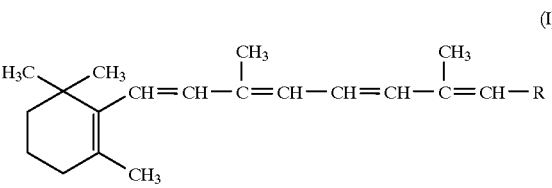

(I)

wherein R is —CHO, —CH$_2$OH, —COOH, —CH(R$^1$) (R$^{1''}$), —CH$_2$OR$^2$, —COOR$^3$, —CONHR$^4$ or CON(R$^{4'}$)(R$^{4''}$ in which the groups R$^1$ and R$^{1''}$ are independently lower alkoxy or R$^{1'}$ and R$^{1''}$ taken together are lower alkylenedioxy, R$^2$ is alkanoyl or aroyl, R$^3$ is alkyl, aryl or aralkyl, and R$^4$, R$^{4'}$ and R$^{4''}$ are independently hydrogen, alkyl, aryl or aralkyl.

In the scope of the above definition the term "lower alkoxy" is an alkoxy group with 1 to 6 carbon atoms, such as, for example, methoxy, ethoxy or propoxy. "Lower alkylenedioxy" is such a group which likewise contains 1 to 6 carbon atoms, e.g., methylenedioxy or ethylenedioxy. In both cases the alkyl or alkylene part can be straight-chain or branched depending on the number of carbon atoms. The term "alkanoyl" is not only straight-chain, but also branched alkanoyl groups with 1–18 carbon atoms, such as, for example, formyl, acetyl, propionyl, butyryl, stearoyl and palmitoyl. The term "aroyl" is derived from aromatic carboxylic acids with 7 and 11 carbon atoms and accordingly is benzoyl or naphthoyl, respectively.

The term "alkyl" is a straight-chain or branched alkyl group with 1 to 18 carbon atoms, e.g., methyl, ethyl, propyl, butyl, decyl, dodecyl, hexadecyl or octadecyl. The term "aryl" as such or as part of "aralkyl" is phenyl or naphthyl. Finally, the term "aralkyl" embraces such groups with 1 to 4 carbon atoms in the aliphatic part, e.g., benzyl and phenylpropyl.

Vitamin A acetate or vitamin A acid is preferably used as the vitamin A compound.

A Z isomer of a vitamin A compound to be isomerized, e.g., the 9-Z, the 11-Z, the 13-Z, the 9,13-di-Z or the 11,13-di-Z isomer, can be isomerized individually starting from the pure isomer or as a component of a mixture of several of such Z isomers, whereby in a mixture already to some extent the all-E isomer, and the 13-Z isomer which by necessity is present in equilibrium with this all-E isomer and/or impurities can also be present. Furthermore, several vitamin A compounds can be present as isomers in a mixture to be isomerized. A typical example of such a mixture results from the multi-stage production of a vitamin A compound, e.g., vitamin A acetate: after several stages there is obtained by crystallization and filtration a crystallizate containing an all E-vitamin A compound and a mother liquor.

In addition to impurities, this mother liquor contains not only the all-E isomer, but also Z isomers of the desired vitamin A compound, whereby the amount of isomerizable Z isomers may be considerable. This mixture, or the mother liquour remaining after removal of most of the impurities, can be subjected to the isomerization process in accordance with the invention. After carrying out the isomerization process in accordance with the invention and removing the all-E isomer there is obtained a mixture which is rich in the 13-Z isomer, from which, if desired, the 13-Z isomer can likewise be removed.

The catalyzed isomerization in accordance with the invention is preferably effected in an inert solvent, even when the isomer or isomer mixture to be isomerized is liquid at the process temperature. The inert solvent used is not critical. As solvents there come into consideration not only polar organic solvents, e.g., acetonitrile and dimethylformamide (aprotic polar solvents), but also apolar organic solvents, such as aliphatic and aromatic hydrocarbons, e.g., pentane, hexane, heptane, benzene, toluene, xylene and petroleum ether; and halogenated aliphatic and aromatic hydrocarbons, e.g., methylene chloride, ethylene chloride, chloroform, carbon tetrachloride and chlorobenzene. Other polar organic solvents which come into consideration are lower aliphatic alcohols, e.g., methanol, ethanol and propanol (protic polar solvents) and lower aliphatic esters, e.g., methyl acetate and ethyl acetate (aprotic polar solvents). Solvent mixtures, even in combination with small amounts of water, can also be used. The aliphatic hydrocarbons, especially hexane, and the lower aliphatic alcohols, especially ethanol, are especially preferred solvents.

Insofar as a substance to be isomerized is present in liquid form, the isomerization can also be carried out in the absence of a solvent. However, the use of a solvent is preferred having regard to a subsequent crystallization.

Preferred solutions used in the isomerization are those having a concentration up to 90 wt. % (weight of vitamin A compounds to total weight (including solvent, if present)), especially about 5 wt. % to about 80 wt. %. About 50 wt. % to 70 wt. % solutions are especially preferred, since these represent the best conditions for the subsequent crystallization of the all-E isomer.

The catalytic contact with NO is conveniently effected by introducing NO or a gas mixture containing NO into the mixture containing the vitamin A compound to be isomerized and dispersing the NO or the gas mixture containing NO. This contact may be carried out by any conventional means, e.g., by rotating the gas stream, at atmospheric pressure or under a slight over-pressure. Pressures up to 1000 kPa above atmospheric pressure, especially pressures of about 10 kPa to about 300 kPa above atmospheric pressure, are preferred. When gas mixtures containing NO are used for the catalysis, these should contain 1 to about 90 wt. % NO (weight of NO to weight of mixture). Gas mixtures with 10 to 80 wt. % NO, especially with 10 to 60 wt. % NO, are preferably used. Inert gases, such as, for example, nitrogen, helium, argon, carbon dioxide, dinitrogen monoxide, methane and ethane, are suitable for the production of the NO gas mixture. Nitrogen, which is simultaneously employed to provide an inert atmosphere over the reaction mixture, is preferably used.

The temperature at which the isomerization of the invention is carried out is not critical. Any temperature at which at least some isomerization occurs up to about 200° C. may be used. The process is preferably effected at temperatures up to about 150° C., especially up to about 100° C. It is especially preferred to carry out the process at temperatures in the range of about 30° C. to about 80° C. The isomerization can also be effected at room temperature and thereunder. Conveniently, in the isomerization the concentration and temperature are chosen such that the all-E isomer formed is separated continuously; this can be effected in a manner known per se.

The isomerization period is not critical so long as some isomerization occurs. The isomerization period is generally between about 1 minute and about 50 hours, especially between about 10 minutes and about 30 hours, preferably between about 30 minutes and about 20 hours. The isomerization period is largely dependent on the chosen temperature and the NO pressure. In the case of long isomerization periods, low temperatures and low NO pressures produce the same or similar results as high temperatures and correspondingly shorter isomerization periods. Since, as is known, vitamin A compounds are relatively unstable compounds, the reaction conditions are preferably chosen such that the reaction mixture need not be heated to high temperatures for a long period.

The isomerization is preferably effected with the exclusion of air, i.e., under an inert gas, e.g., nitrogen or argon. Moreover, the isomerization can be carried out not only discontinuously, but also continuously.

After completion of the isomerization process the isolation of the desired all-E- or 13-Z-vitamin A compound can be carried out according to methods known per se, such as, for example, cooling crystallization or evaporation crystallization. Thereby, for a separation which is as complete as possible the clear differences in solubility behaviour between the isomers to be isolated and the remaining isomers (including impurities) may be used to advantage.

The isomerization process in accordance with the invention is illustrated by the following Examples; in the Examples all analyses given have been carried by high pressure liquid chromatography (HPLC).

EXAMPLE 1

49 g of a mixture containing 23% all-E-vitamin A acetate, 39% 13-Z-vitamin A acetate, 18% 11-Z-vitamin A acetate, 5% 11,13-di-Z-vitamin A acetate and 3% 9-Z- and/or 9,13-di-Z-vitamin A acetate (remainder impurities) are dissolved in 35 ml of methyl acetate under argon in a sulphonation flask. Pure NO gas is then conducted into this solution while stirring for 10 minutes. Subsequently, the reaction apparatus is completely closed and the solution is stirred intensively at room temperature for 5 hours. Subsequently, the NO atmosphere is replaced by inert gas. A mixture containing 43% all-E-, 26% 13-Z-, 12% 11-Z-, 4% 11,13-di-Z- and 3% 9-Z- and/or 9,13-di-Z-vitamin A acetate is obtained.

EXAMPLE 2

200 g of a mixture containing 23% all-E-, 40% 13-Z-, 17% 11-Z-, 5% 11,13-di-Z- and 3% 9-Z- and/or 9,13-di-Z-vitamin A acetate are dissolved in 140 ml of hexane under nitrogen in a pressure-tight apparatus. After flushing the apparatus with nitrogen at atmospheric pressure NO gas is introduced at room temperature while stirring to an over-pressure of 0.5 bar (50 kPa) and the apparatus is closed. The solution is heated to 40° C. while stirring and stirred intensively for 5 hours. Subsequently, the apparatus is de-pressurized and cooled to room temperature. A mixture containing 48% all-E-, 24% 13-Z-, 4% 11-Z-, 4 % 11,13-di-Z- and 3% 9-Z- and/or 9,13-di-Z-vitamin A acetate is obtained.

EXAMPLE 3

100 g of a mixture containing 23% all-E-, 32% 13-Z-, 15% 11-Z-, 6% 11,13-di-Z- and 3% 9-Z- and/or 9,13-di-Z-vitamin A acetate are placed without solvent under nitrogen in a pressure-tight apparatus. After flushing the apparatus with nitrogen at atmospheric pressure NO gas is introduced at room temperature while stirring to an over-pressure of 0.5 bar (50 kPa) and the apparatus is closed. The liquid is heated to 40° C. while stirring and stirred intensively for 5 hours. Subsequently, the apparatus is de-pressurized and cooled to room temperature. A mixture containing 48% all-E-, 21% 13-Z-, 2% 11-Z-, 5 % 11,13-di-Z- and 3% 9-Z- and/or 9,13-di-Z-vitamin A acetate is obtained.

EXAMPLE 4

19 g of a mixture containing 94% all-E-vitamin A acetate and 3% 13-Z-vitamin A acetate are dissolved in 38 g of ethanol under nitrogen in a pressure-tight apparatus. After flushing the apparatus with nitrogen at atmospheric pressure NO gas is introduced at room temperature while stirring to an over-pressure of 0.5 bar (50 kPa) and the apparatus is closed. The solution is heated to 40° C. while stirring and stirred intensively for 5 hours. Subsequently, the apparatus is depressurized and cooled to room temperature. A mixture containing 67% all-E-vitamin A acetate and 28% 13-Z-vitamin A acetate is obtained. The content of the other isomers (11-Z-, 11,13-di-Z- and 9-Z-and/or 9,13-di-Z-vitamin A acetate) is significantly below 1%.

I claim:

1. A process for the catalyzed isomerization of a Z isomer of a vitamin A compound into a mixture of the all-E and 13-Z isomers of the vitamin A compound, which process comprises contacting a reaction mixture comprising the Z isomer of the vitamin A compound with nitrogen monoxide under conditions of temperature and NO pressure sufficient to isomerize the Z isomer to the mixture of the all-E and 13-Z isomers.

2. The process of claim 1 wherein the vitamin A compound is vitamin A, vitamin A aldehyde, vitamin A acid or a derivative thereof.

3. The process of claim 2 wherein the vitamin A compound is of the formula:

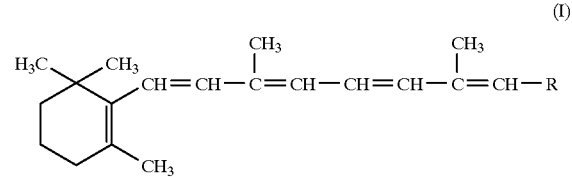

wherein R is —CHO, —CH$_2$OH, —COOH, —CH(R$^{1'}$)(R$^{1''}$), —CH$_2$OR$^2$, —COOR$^3$, —CONHR$^4$ or CON(R$^{4'}$)(R$^{4''}$), in which the groups R$^{1'}$ and R$^{1''}$ are independently lower alkoxy or R$^{1'}$ and R$^{1''}$ taken together are lower alkylenedioxy, R$^2$ is alkanoyl or aroyl, R$^3$ is alkyl, aryl or aralkyl, and R$^4$, R$^{4'}$ and R$^{4''}$ are independently hydrogen, alkyl, aryl or aralkyl.

4. The process of claim 3 wherein the Z isomer is a 9-Z, an 11-Z, a 13-Z, a 9,13-di-Z or a 11,13-di-Z isomer of a vitamin A compound.

5. The process of claim 4 wherein the vitamin A compound is vitamin A acetate or vitamin A acid.

6. The process of claim 5 wherein the NO pressure is in the range from atmospheric pressure to about 1000 kPa above atmospheric pressure.

7. The process of claim 6 wherein the temperature is in the range from about 30° C. to about 80° C.

8. The process of claim 7 wherein the reaction mixture further comprises a polar or apolar organic solvent.

9. The process of claim 8 wherein the solvent is an aliphatic hydrocarbon or a lower aliphatic alcohol.

10. The process of claim 9 wherein the NO pressure is in the range from about 10 kPa to about 300 kPa above atmospheric pressure.

11. The process of claim 10 wherein the solvent is hexane or ethanol.

12. The process of claim 11 wherein the nitrogen monoxide is present as a 10 to 60 wt. % mixture with nitrogen.

* * * * *